United States Patent [19]

Martin et al.

[11] Patent Number: 5,430,038
[45] Date of Patent: Jul. 4, 1995

[54] 2-(4-PYRRLIDINYL)-1H-PYRIDO[4,3-B]INDOL-1-ONES AND RELATED COMPOUNDS

[75] Inventors: Lawrence L. Martin, Lebanon; Denise M. Flanagan, Livingston; Joseph F. Payack, Somerset, all of N.J.

[73] Assignee: Hoechst-Roussel Pharmaceuticals Inc., Somerville, N.J.

[21] Appl. No.: 148,305

[22] Filed: Nov. 8, 1993

Related U.S. Application Data

[62] Division of Ser. No. 67,891, May 27, 1993, Pat. No. 5,292,883, which is a division of Ser. No. 821,364, Jan. 15, 1992, Pat. No. 5,229,517, which is a division of Ser. No. 588,870, Sep. 27, 1990, Pat. No. 5,102,889.

[51] Int. Cl.$^6$ .................. A61K 31/44; C07D 47/06
[52] U.S. Cl. .................. 514/292; 514/212; 540/597; 540/599; 540/602; 546/86
[58] Field of Search .......... 514/212, 292; 540/597, 540/602, 599; 546/86

[56] References Cited

U.S. PATENT DOCUMENTS

| | | | |
|---|---|---|---|
| 3,991,199 | 11/1976 | Berger | 546/85 |
| 4,148,895 | 4/1979 | Lattrell | 514/419 |
| 4,432,978 | 2/1984 | Welch | 514/292 |
| 4,977,159 | 12/1990 | Sevrin | 514/292 |
| 5,013,733 | 5/1991 | Coates | 514/213 |
| 5,183,820 | 2/1993 | Coates | 514/292 |

FOREIGN PATENT DOCUMENTS

| | | |
|---|---|---|
| 0306323 | 3/1989 | European Pat. Off. |
| 0353983 | 2/1990 | European Pat. Off. |
| 0385722 | 9/1990 | European Pat. Off. |
| 2055372 | 3/1981 | United Kingdom |

OTHER PUBLICATIONS

Berger "Medicinal Chemistry" pp. 871–872 John Wiley and Sons, (1982).

Merk Index, Merk Publications, pp. 599, 1208 9th Edition, 1976.

G. A. Bahadur, et al., Journal Chemical Society, Perkin I, 1688 (1980), published in Great Britain and entitled "Reactions of 4,5-Dihydro-5-methylpyrano[4,3-b]indole-1,3-dione: a Synthesis of N-Methylisotryptophol".

"Comprehensive Organic Chemistry—The Synthesis and Reactions of Organic Compounds" D. Barton and W. D. Ollis, Editors, vol. 2, Pergamon Press, New York, N.Y., 1979, pp. 34 to 38 and 994 to 999.

"Burger's Medicinal Chemistry", 4th Edition, Part I., The Basis of Medicinal Chemistry, M. E. Wolf, Editor, John Wiley and Sons, New York, N.Y., pp. 55 to 105 (1982).

*Primary Examiner*—Celia Chang
*Attorney, Agent, or Firm*—Raymond R. Wittekind

[57] ABSTRACT

Novel 2-(4-piperidinyl)-1H-pyrido[4,3-b]indol-1-ones and related compounds, intermediates and processes for the preparation thereof, and methods of treating psychoses employing compounds and compositions thereof are disclosed.

3 Claims, No Drawings

2-(4-PYRRLIDINYL)-1H-PYRIDO[4,3-B]INDOL-1-ONES AND RELATED COMPOUNDS

This is a division of application Ser. No. 08/067,891 filed May 27, 1993, now U.S. Pat. No. 5,292,883, which is a division of application Ser. No. 07/821,364 filed Jan. 15, 1992, now U.S. Pat. No. 5,229,514, which is a division of application Ser. No. 07/588,870 filed Sep. 27, 1990, now U.S. Pat. No. 5,102,889.

DESCRIPTION OF THE INVENTION

The present invention relates to novel 1H-pyrido[4,3-b]indol-1-ones. More particularly, the present invention relates to 2-(4-piperidinyl)-1H-pyrido[4,3-b]indol-1-ones and related compounds of formula 1.

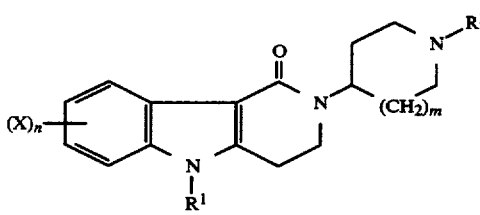

wherein $R^1$ is hydrogen, loweralkyl, phenyl, phenyl substituted by one or more loweralkyl, loweralkoxy, halogen, or trifluoromethyl groups, phenylloweralkyl or phenylloweralkyl in which the phenyl group is substituted by one or more loweralkyl, loweralkoxy, halogen, or trifluoromethyl groups;

$R^2$ is hydrogen, loweralkyl, furanylloweralkyl, thienylloweralkyl, pyrrolylloweralkyl, pyridinylloweralkyl, phenylloweralkyl, phenylloweralkyl in which the phenyl group is substituted by one or more loweralkyl, loweralkoxy, halogen, or trifluoromethyl groups, or a group of the formula $$\overset{O}{\underset{}{\overset{\|}{C}}}OR^3$$

wherein $R^3$ is loweralkyl, haloloweralkyl, phenyl, phenyl substituted by one or more loweralkyl, loweralkoxy, halogen, or trifluoromethyl groups, phenylloweralkyl or phenylloweralkyl in which the phenyl group is substituted by one or more loweralkyl, loweralkoxy, halogen, or trifluoromethyl groups;

X is hydrogen, loweralkyl, loweralkoxy, halogen, or trifluoromethyl;

m is 0, 1, or 2;

n is 1 or 2; or an optical isomer thereof, or a pharmaceutically acceptable salt thereof, which are useful for treating psychoses, alone or in combination with inert adjuvants.

Preferred 2-(4-piperidinyl-1H-pyrido[4,3-b]indol-1-ones and related compounds are those wherein $R^2$ is hydrogen, phenylloweralkyl or phenylloweralkyl in which the phenyl group is substituted by one or more loweralkyl, loweralkoxy, halogen, or trifluoromethyl groups; and m is 1.

Subgeneric thereto are 1H-pyrido[4,3-b]indol-1-ones wherein $R^2$ is a group of the formula $$\overset{O}{\underset{}{\overset{\|}{C}}}OR^3$$

wherein $R^3$ is haloloweralkyl and m is 1.

The present invention also relates to indoles of formulas 2, 3, and 4

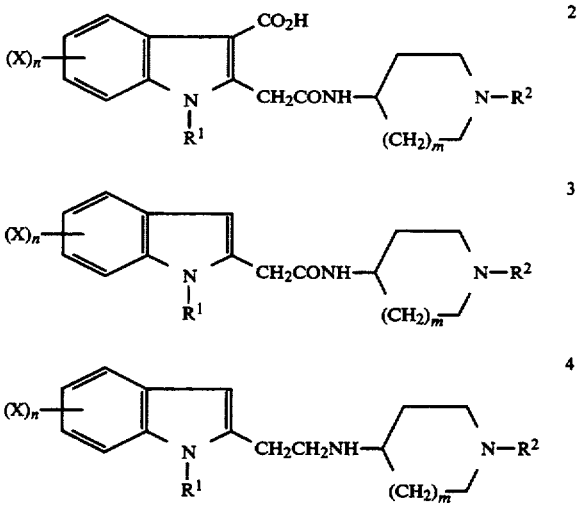

wherein $R^1$ is hydrogen, loweralkyl, phenyl, phenyl substituted by one or more loweralkyl, loweralkoxy, halogen, or trifluoromethyl groups, phenylloweralkyl or phenylloweralkyl in which the phenyl group is substituted by one or more loweralkyl, loweralkoxy, halogen, or trifluoromethyl groups;

$R^2$ is loweralkyl, furanylloweralkyl, thienylloweralkyl, pyrrolylloweralkyl, pyridinylloweralkyl, phenylloweralkyl, or phenylloweralkyl in which the phenyl group is substituted by one or more loweralkyl, loweralkoxy, halogen, or trifluoromethyl groups;

X is hydrogen, loweralkyl, loweralkoxy, halogen, or trifluoromethyl;

m is 0, 1 or 2;

n is 1 or 2; or an optical isomer thereof, or a salt thereof, which are useful as intermediates for the synthesis of the ultimate 2-(4-piperidinyl)-1H-pyrido[4,3-b]indol-1-ones and related compounds of formula 1.

Preferred intermediates 2, 3, and 4 are those wherein $R^2$ is phenylloweralkyl; and m is 1.

As used throughout the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy and the like; the term "halogen" refers to a member of a family consisting of chlorine, fluorine, bromine or iodine. The term "lower"

as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof. The formulas of the compounds shown herein are intended to encompass all possible optical isomers of the compounds so depicted.

The novel 2-(4-piperidinyl)-1H-pyrido[4,3-b]indol-1-ones and related compounds of the present invention are prepared by condensing a pyrano[4,3-b]indol-1,3-dione 5, the preparation of which is described in G. A. Bahadur, et al., Journal Chemical Society Perkin I, 1688 (1980), with an amine of formula 11

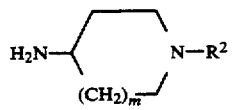

11 wherein
R$^2$ is loweralkyl, furanylloweralkyl, thienylloweralkyl, pyrrolylloweralkyl, pyridinylloweralkyl, phenylloweralkyl, or phenylloweralkyl in which the phenyl group is substituted by one or more loweralkyl, loweralkoxy, halogen, or trifluoromethyl groups and m is as defined above to an indoleacetamidocarboxylic acid 6, which is decarboxylated to an indoleacetamide 7, and, in turn, reduced to an indolylethanamine 8 and cyclized to an indolone 1.

The condensation is conveniently performed by contacting a pyranoindole 5 with an amine 11 in a solvent, for example, an alkanol such as methanol, ethanol, 1- or 2-propanol, or 1,1-dimethylethanol, ethanol being preferred. The condensation temperature is not critical. It is preferred, however, to perform the condensation at the reflux temperature of the reaction medium to assure a reasonable rate of ring opening.

The decarboxylation of an indolecarboxylic acid 6 to an indoleacetamide 7 is accomplished by heating the carboxylic acid 6 to its melting point and maintaining the melt at this temperature until the evolution of carbon dioxide ceases.

The reduction of an indoleacetamide 7 to an indoleethanamine 8 is effected by treating an acetamide 7 with a complex metal hydride in an ethereal solvent. Among complex metal hydrides are alkali metal aluminum hydrides such as lithium aluminum hydride and sodium aluminum hydride. Among ethereal solvents are diethyl ether, 1,2-dimethyoxyethane, 2-methoxyethyl ether, tetrahydrofuran, and dioxane, and combinations thereof. A reduction promoter, for example, an aluminum trihalide such as aluminum trichloride may be employed to facilitate the reaction. The preferred reduction medium consists of lithium aluminum hydride in tetrahydrofuran/ether containing aluminum chloride. The initial phase of the reduction, i.e., the mixing of the acetamide 7, complex metal hydride, and reduction promoter is preferably performed at a reduced temperature of about 0° C. The reduction is completed at about 25° C.

The cyclization of an indoleethanamine 8 to a 1H-pyrido[4,3-b]indol-1-one 1 is achieved by treating an ethanamine 8 with a compound of the formula

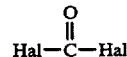

12 wherein
Hal is chloro or bromo in a suitable solvent at a temperature within a noncritical temperature range of about 0° C. to about 50° C., a temperature of about 25° C. being preferred. Among suitable solvents there may be mentioned aromatic solvents, for example, benzene, and toluene, and halocarbons, for example, dichloromethane, trichloromethane, and 1,1- and 1,2-dichloroethane, and combinations thereof. Phosgene, i.e., a compound of formula 12 wherein Hal is chloro is the preferred cyclizing agent. A combination of aromatic and halocarbon solvents is preferred. A combination of toluene and dichloromethane is most preferred.

To prepare a 1H-pyrido[4,3-b]indol-1-one of formula 10, i.e., an indolone of formula 1 wherein R$^2$ is hydrogen, an indolone 1 wherein R$^2$ is phenylmethyl or substituted phenylmethyl is acylated to an N-haloalkoxycarbonylpiperidinylindolone 9 wherein R$^3$ is haloloweralkyl and R$^1$, X, m, and n are as hereinbeforedescribed, which is cleaved to 10.

The acylation is carried out by contacting indolone 1 (R$^2$ is phenylmethyl or substituted phenylmethyl) with a haloloweralkylhaloformate of formula 13

13 wherein
R$^3$ is haloloweralkyl and Hal is chloro or bromo in a halocarbon such as dichloromethane, trichloromethane, or 1,1-dichloro- or 1,2-dichloroethane, preferably at the reflux temperature of the reaction medium. 1,2-Dichloroethane is the preferred solvent.

The cleavage of a haloloweralkoxycarbonylpiperidinylindolone 9 to a piperidinylindolone 10 is conducted in an alkanol such as methanol, ethanol, 1- or 2-propanol, or 1,1-dimethylethanol, methanol being preferred, at a temperature from about 25° C. to the reflux temperature of the reaction medium, the reflux temperature being preferred.

While the synthesis of the compounds of the present invention is described for the piperidinyl derivatives (wherein m is 1 ), the pyrrolidinyl (wherein m is 0) and azepinyl (wherein m is 2) derivatives may be prepared by substantially similar processes.

The 2-(4-piperidinyl)-1H-pyrido[4,3-b]indol-1-ones and related compounds of the present invention are useful for treating psychoses by vitue of their ability to elicit an antipsychotic response in mammals.

Antipsychotic activity is determined in the climbing mice assay by methods similar to those described by P. Protais et al., Psychopharmacol., 50, 1(1976) and B. Costall, Eur. J. Pharmacol., 50, 39(1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior | Score |
| --- | --- |
| Mice with: | |
| 4 paws on bottom (no climbing) | 0 |
| 2 paws on the wall (rearing) | 1 |
| 4 paws on the wall (full climb) | 2 |

Mice consistently climbing before the injection of apormorphine are discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score; 6 per mouse over 3 readings) and the total score of the control group (vehicle intraperitioneally-apomorphine subcutaneously) is set to 100%. $ED_{50}$ values with 95% confidence limits are calculated by a linear regression analysis. Antipsychotic activity expressed as the $ED_{50}$ value of representative 2-(4-piperidinyl)-1H-pyrido[4,3-b]indolones and related compounds as well as two standard antipsychotics are presented in Table I.

TABLE I

| Compound | Antipsychotic Activity $ED_{50}$ (mg/kg, ip) |
| --- | --- |
| 5-methyl-2-[1-(phenyl-methyl)-4-piperidinyl]-2,3,4,5-tetrahydro-1H-pyrido[4,3-b]indol-1-one | 4.6 |
| haloperidol (standard) | 0.14 |
| thioridazine | 3.6 |

Antipsychotic activity is achieved when the present 2-(4-piperidinyl)-1H-pyrido[4,3-b]indolones and related compounds are administered to a subject requiring such treatment as effective oral, parenteral or intravenous dose of from 0.01 to 50 mg/kg of body weight per day. A particularly preferred effective range is about 1 to 5 mg/kg of body weight per day. It is to be understood, however, that for any particular subject, specific dosage regimens should be adjusted to the individual need and the professional judgment of the person administering or supervising the administration of the aforesaid compound. It is to be further understood that the dosages set forth herein are exemplary only and they do not, to any extent, limit the scope or practice of the invention.

Antagonism of apomorphine-induced stereotypy is a property of many antipsychotics. Antipsychotics displaying little effect in this assay would be expected to show a low propensity to cause undesirable extrapyramidal side effects and/or tardive dyskinesias in mammals. Antagonism of apomorphine-induced stereotypy of the present 2-(4-piperidinyl)-1H-pyrido[4,3-b]indol-1-ones is determined by methods similar to those described by N. E. Anden, et al., J. Pharma. Pharmacol., 19, 627, (1967) and A. M. Ernst, et al., Psychopharmacologia (Berl.), 10, 316, (1967).

Groups of male Wistar rats (125-200 grams) are used and food and water are available ad libitum. Drugs are prepared using distilled water and, if insoluble, a suitable surfactant is added. The route of administration may be varied and the dosage volume is 10 ml/kg. For a primary screen, a group size of six is used. Drug is administered one hour prior to scoring and the animals are placed in individual clear plastic cages (24×14×13 cm). The control group receives vehicle. Apomorphine hydrochloride solution is prepared at a concentration of 1.5 mg/10 ml in a 0.03% ascorbic acid stock solution (30 mg of ascorbic acid in 100 ml of 1% saline) to increase the stability of the apomorphine hydrochloride while in solution. Apomorphine hydrochloride solution is administered at a dose of 1.5 mg/kg subcutaneous (s.c.) with a dosage volume of 1 ml/kg. Fifty minutes after drug dosing, stereotypic behavior is noted. Stereotypic activity is defined as sniffing, licking or chewing behavior that occurs in a repetitive manner and is rated as follows: Constant sniffing, licking or chewing without interruption; the animal is considered protected if this behavior is interrupted.

The percent effectiveness of a drug is determined by the number of animals protected in each group.

A dose-response is run in the same manner as a primary screen except that a group size of 10 is used and the animals are dosed in a randomized manner. One group receives vehicle. $ED_{50}$ for stereotypy are calculated by means of probit analysis.

Inhibition of apomorphine-induced stereotypy by a representative 2-(4-piperidinyl)-1H-pyrido[4,3-b]indolone of the present invention and two standards is given in Table II.

TABLE II

| Compounds | Dose (mg/kg, ip) body wt.) | % Inhibition of Apomorphine-Induced Stereotype |
| --- | --- | --- |
| 5-methyl-2-[1-(phenylmethyl)-4-piperidinyl]-2,3,4,5-tetrahydro-1H-pyrido[4,3-b]indol-1-one | 24 | 50 |
| haloperidol | 0.2 | 50 |
| thioridazine | 38 | 50 |

Compounds of the invention include:

a.         8-ethyl-5-methyl-2-[1-(phenylmethyl)-4-piperidinyl]-2,3,4,5-tetrahydro-1H-pyrido[4,3-b]indol-1-one;

b.         7-ethoxy-5-methyl-2-[1-(phenylmethyl)-4-piperidinyl]-2,3,4,5-tetrahydro-1H-pyrido[4,3-b]indol-1-one;

c.     7,8-dichloro-5-methyl-2-[1-(phenylmethyl)-4-piperidinyl]-2,3,4,5-tetrahydro-1H-pyrido[4,3-b]indol-1-one;

d.         6-bromo-5-methyl-2-[1-(phenylmethyl)-4-piperidinyl]-2,3,4,5-tetrahydro-1H-pyrido[4,3-b]indol-1-one;

e.     5-methyl-2-[1-(phenylmethyl)-4-piperidinyl]-2,3,4,5-tetrahydro-9-trifluoromethyl-1H-pyrido[4,3-b]indol-1-one;

f.     5-methyl-2-[1-phenylmethyl)-3-pyrrolidinyl]-2,3,4,5-tetrahdyro-1H-pyrido[4,3-b]indol-1-one;

g. 5-methyl-2-[1-(phenylmethyl)-4-(2,3,4,5,6,7-hexahydroazepinyl)]-2,3,4,5-tetrahydro-1H-pyrido[4,3-b]indol-1-one;
h. 5-methyl-2-[1-(4-ethylphenylmethyl)-4-piperidinyl]-2,3,4,5-tetrahydro-1H-pyrido[4,3-b]indol-1-one;
i. 5-methyl-2-[1-(4-ethoxyphenylmethyl)-4-piperidinyl]-2,3,4,5-tetrahydro-1H-pyrido[4,3-b]indol-1-one;
j. 5-methyl-2-[1-(5-chlorophenylmethyl)-4-piperidinyl]-2,3,4,5-tetrahydro-1H-pyrido[4,3-b]indol-1-one;
k. 5-methyl-2-[1-(3,4-dichlorophenylmethyl)-4-piperidinyl]-2,3,4,5-tetrahydro-1H-pyrido[4,3-b]indol-1-one;
l. 5-methyl-2-[1-(4-trifluoromethylphenylmethyl)-4-piperidinyl]-2,3,4,5-tetrahydro-1H-pyrido[4,3-b]indol-1-one;
m. 5-methyl-2-(4-piperidinyl)-2,3,4,5-tetrahyro-1H-pyrido[4,3-b]indol-1-one;
n. 5-methyl-2-(1-methyl-4-piperidinyl)-2,3,4,5-tetrahydro-1H-pyrido[4,3-b]indol-1-one;
o. 2-(4-piperidinyl)-2,3,4,5-tetrahydro-1H-pyrido[4,3-b]indol-1H-one;
p. 5-phenyl-2-(4-piperidinyl)-2,3,4,5-tetrahydro-1H-pyrido[4,3-b]indol-1-one;
q. 2-(4-piperidinyl)-5-(2-methylphenyl)-2,3,4,5-tetrahydro-1H-pyrido[4,3-b]indol-1-one;
r. 2-(4-piperidinyl)-5-(4-chlorophenyl)-2,3,4,5-tetrahydro-1H-pyrido[4,3-b]indol-1-one;
s. 2-(4-piperidinyl)-5-(3-methoxyphenyl)-2,3,4,5-tetrahydro-1H-pyrido[4,3-b]indol-1-one;
t. 5-(4-trifluoromethyl)-2-(piperidinyl)-2,3,4,5-tetrahydro-1H-pyrido[4,3-b]indol-1-one;
u. 5-(phenylethyl)-2-(piperidinyl)-2,3,4,5-tetrahydro-1H-pyrido[4,3-b]indol-1-one;
v. 5-[(2-chlorophenyl)methyl]-2-(piperidinyl)-2,3,4,5-tetrahydro-1H-pyrido[4,3-b]indol-1-one;
w. 5-[(4-methylphenyl)methyl]-2-(piperidinyl)-2,3,4,5-tetrahydro-1H-pyrido[4,3-b]indol-1-one;
x. 5-[(3-methoxyphenyl)methyl]-2-(piperidinyl)-2,3,4,5-tetrahydro-1H-pyrido[4,3-b]indol-1-one;
y. 2-(piperidinyl)-5-[(3-trifluoromethyl)methyl]-2,3,4,5-tetrahydro-1H-pyrido[4,3-b]indol-1-one;
z. 5-methyl-2-[1-(2-furanylmethyl)-4-piperidinyl]-2,3,4,5-tetrahydro-1H-pyrido[4,3-b]indol-1-one;
a'. 5-methyl-2-[1-(3-thienylmethyl)-4-piperidinyl]-2,3,4,5,-tetrahydro-1H-pyrido[4,3-b]indol-1-one;
b'. 5-methyl-2-[1-(2-pyrrolylmethyl)-4-piperidinyl]-2,3,4,5-tetrahydro-1H-pyrido[4,3-b]indol-1-one;
c'. 5-methyl-2-[1-(3-pyridinylmethyl)-4-piperidinyl]-2,3,4,5-tetrahydro-1H-pyrido[4,3-b]indol-1-one;
d'. 2-[1-(methylcarbamoyl)-4-piperidinyl]-5-methyl-2,3,4,5-tetrahydro-1H-pyrido[4,3-b]indol-1-one;
e'. 2-[1-(phenylcarbamoyl)-4-piperidinyl]-5-methyl-2,3,4,5-tetrahydro-1H-pyrido[4,3-b]indol-1-one;
f'. 2-[1-(2-chlorophenylcarbamoyl)-4-piperidinyl]-5-methyl-2,3,4,5-tetrahydro-1H-pyrido[4,3-b]indol-1-one;
g'. 2-[1-(2-methylphenylcarbamoyl)-4-piperidinyl]-5-methyl-2,3,4,5-tetrahydro-1H-pyrido[4,3-b]indol-1-one;
h'. 2-[1-(2-methoxyphenylcarbamoyl)-4-piperidinyl]-5-methyl-2,3,4,5-tetrahydro-1H-pyrido[4,3-b]indol-1-one;
i'. 5-methyl-2,3,4,5-tetrahydro-2-[1-(3-trifluoromethylphenylcarbamoyl)-1H-pyrido[4,3-b]indol-1-one;
j'. 1H-indole-2-[N-(phenylmethyl-4-piperidinyl)acetamido]-3-carboxylic acid;
k'. 1H-indole-2-[N-(phenylmethyl-4-piperidinyl)acetamido]-3-carboxylic acid;
l'. 2-(1-methyl-1H-indol-2-yl)-N-[1-(2-methylphenyl)methyl-4-piperidinyl]ethanamine;
m'. N-[1-(4-methoxyphenyl)methyl-4-piperidinyl]-2-(1-methyl-1H-indol-2-yl)ethanamine;
n'. N-[1-(2-bromophenyl)methyl-4-piperidinyl]-2-(1-methyl-1H-indol-2-yl)ethanamine;
o'. 2-(1-methyl-1H-indol-2-yl)-N-[1-(3-trifluoromethylphenyl)methyl-4-piperidinyl]ethanamine;
p'. 2-[N-[1-(2-furanyl)methyl]-4-piperidinylacetamido]-1H-indole-1-methyl-3-carboxylic acid;
q'. 1H-indole-1-methyl-2-[N-[1-(3-thienyl)methyl]-4-piperidinyl]acetamide;
r'. 2-[N-[1-(2-pyrrolyl)methyl]-4-piperidinyl]1H-1-indole-1-methylacetamide; and
s'. 2-(1-methyl-1H-indol-2-yl-N-[1-[3-(pyridinyl)methyl-4-piperidinyl)]ethanamine.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

1H-Indole-1-methyl-2-[N-(phenylmethyl-4-piperidinyl)acetamido]-3-carboxylic acid A solution of 4,5-dihydro-5-methylpyrano[4,3-b]indole-1,3-dione (9.95 g), 4-amino-1-phenylmethylpiperidine (10.55 g), and 95% ethanol (200 ml) was heated under reflux overnight, with stirring. The solution was evaporated and the residue was dissolved in dichloromethane (200 ml). The solution was dried over anhydrous sodium sulfate, filtered, and the filtrate was concentrated. The residue was purified by high performance liquid chromatography (silica gel, eluted with 20%-methanol/dichloromethane). The appropriate fractions were collected, combined, and evaporated. A 5.0 g-portion of the residue was recrystallized from hot methanol to yield 4.4 g (61%) of product, mp 147°-9° C. (dec).

ANALYSIS: Calculated for $C_{24}H_{27}N_3O_3$: 71.09%C 6.71%H 10.36%N Found: 71.22%C 6.83%H 10.37%N

EXAMPLE 2

1H-Indole-1-methyl-2-[N-(1-phenylmethyl-4-piperidinyl)]acetamide

1H-Indole-1-methyl-2-[N-(1-phenylmethyl-4-piperidinyl)acetamido]-3-carboxylic acid (6.66 g) was melted and held at 60° C. for one-half hour, until gas evolution ceased. The melt was purified by high performance liquid chromatography (silica gel, eluted with 10%-methanol/dichloromethane). The appropriate fractions were collected, combined, and evaporated to yield 4.50 g (76%) of product, mp 207°-8° C.

ANALYSIS: Calculated for $C_{23}H_{27}N_3O$: 76.42%C 7.53%H 11.62%N Found: 76.14%C 7.46%H 11.59%N

EXAMPLE 3

2-(1-Methyl-1H-indol-2-yl)-N-(1-phenylmethyl-4-piperidinyl)ethanamine

To a solution of lithium aluminum hydride (1M in tetrahydrofuran, 63 ml) and ether (120 ml) was added over 10 mins aluminum trichloride (8.4 g) at 0° C., under nitrogen, with stirring. The mixture was stirred for 15 mins at 0° C. and 1H-indol-1-methyl-2-[N-(1-phenylmethyl-4-piperidinyl)]acetamide was added. The mixture was stirred at room temperature for 1.5 hrs and was quenched with 1N aqueous sodium hydroxide solution (500 ml), added over 20 mins. The aqueous phase was extracted with dichloromethane (3×250 ml), and the combined organic phase was washed with water (500 ml), brine (500 ml), dried over anhydrous sodium sulfate, filtered, and the filtrate was concentrated. The residue was purified by high performance liquid chromatography (silica gel, 50% methanol/dichloromethane). The appropriate fractions were collected, combined, and evaporated. The residue solidified upon standing. The solid was recrystallized from hot hexane to give 5.9 g of product, mp 72°-73° C.

ANALYSIS: Calculated for $C_{23}H_{29}N_3$: 79.50%C 8.41%H 12.09%N Found: 79.68%C 8.66%H 12.12%N

EXAMPLE 4

5-Methyl-2-[1-(phenylmethyl)-4-piperidinyl]-2,3,4,5-tetrahydro-1H-pyrido[4,3-b]-indole-1-one hydrochloride To a solution of phosgene (1.93M in toluene, 3.58 ml) and dichloromethane (25 ml) was added a solution of 2-(1-methyl-1H-indol-2-yl)-N-(1-phenylmethyl-4-piperidinyl)ethanamine (0.80 g) and dichloromethane (25 ml), with stirring. The mixture was stirred overnight, quenched with water, and basified with sodium hydroxide solution. The phases were separated. The organic phase was washed with water, brine, dried over anhydrous sodium sulfate, filtered, and the filtrate was evaporated. The residue was combined with the residue from a second experiment and purified by high performance liquid chromatography (silica gel column, eluted with 7.5% methanol/dichloromethane). The appropriate fractions were collected, combined, and evaporated to yield 1.25 g (20%) of product, mp 191°-3° C., as the free base.

A solution of the free base and methanol (10 ml) was treated with ethereal hydrogen chloride and diluted with ether. The precipitate was collected, dried, and recrystallized from 1-propanol to afford product, mp 302°-305° C. (dec).

ANALYSIS: Calculated for $C_{24}H_{27}N_3O \cdot HCl$: 70.32%C 6.88%H 10.25%N Found: 70.11%C 6.94%H 10.08%N

EXAMPLE 5

2-[1-(α-Chloroethylcarbamoyl)-4-piperidinyl]-5-methyl-2,3,4,5-tetrahydro-1H-pyrido[4,3-b]indol-1-one To a solution of 5-methyl-2-[1-(phenylmethyl)-4-piperidinyl]-2,3,4,5-tetrahydro-1H-pyrido[4,3,-b]indol-1-one (0.40 g) in dichloromethane (4.0 ml) was added α-chloroethyl chloroformate (0.16 ml) at 0° C., with stirring. The solution was heated under reflux for 3 hrs, under nitrogen, and then stirred at room temperature for 1 hr. The reaction mixture was evaporated under reduced pressure. The residue was dissolved in dichloromethane and washed sequentially with brine, 10% sodium hydroxide solution, and brine. The organic phase was dried over anhydrous sodium sulfate, filtered, and the filtrate was concentrated. The residue was purified by column chromatography (silica gel, 5% methanol/ethyl acetate). The appropriate fractions were collected, combined, and concentrated to yield 0.30 g (70%) of product.

EXAMPLE 6

5-Methyl-2-(4-piperidinyl)-2,3,4,5-tetrahydro-1H-pyrido[4,3-b]indol-1-one dihydrochloride monohydrate 2-[1-(α-Chloroethylcarbamoyl)-4-piperidinyl]-5-methyl-2,3,4,5-tetrahydro-1H-pyrido[4,3-b]indol-1-one (0.300 g) was dissolved in anhydrous methanol (6 ml), and the solution was heated under reflux for 4 hrs. The reaction mixture was evaporated, and the residue was recrystallized from absolute ethanol to afford 0.10 g (50%) of product.

ANALYSIS: Calculated for $C_{17}H_{21}N_3O \cdot 2HCl \cdot H_2O$: 54.56%C 6.73%H 11.23%N Found: 55.03%C 6.69%H 11.20%N

REACTION SCHEME

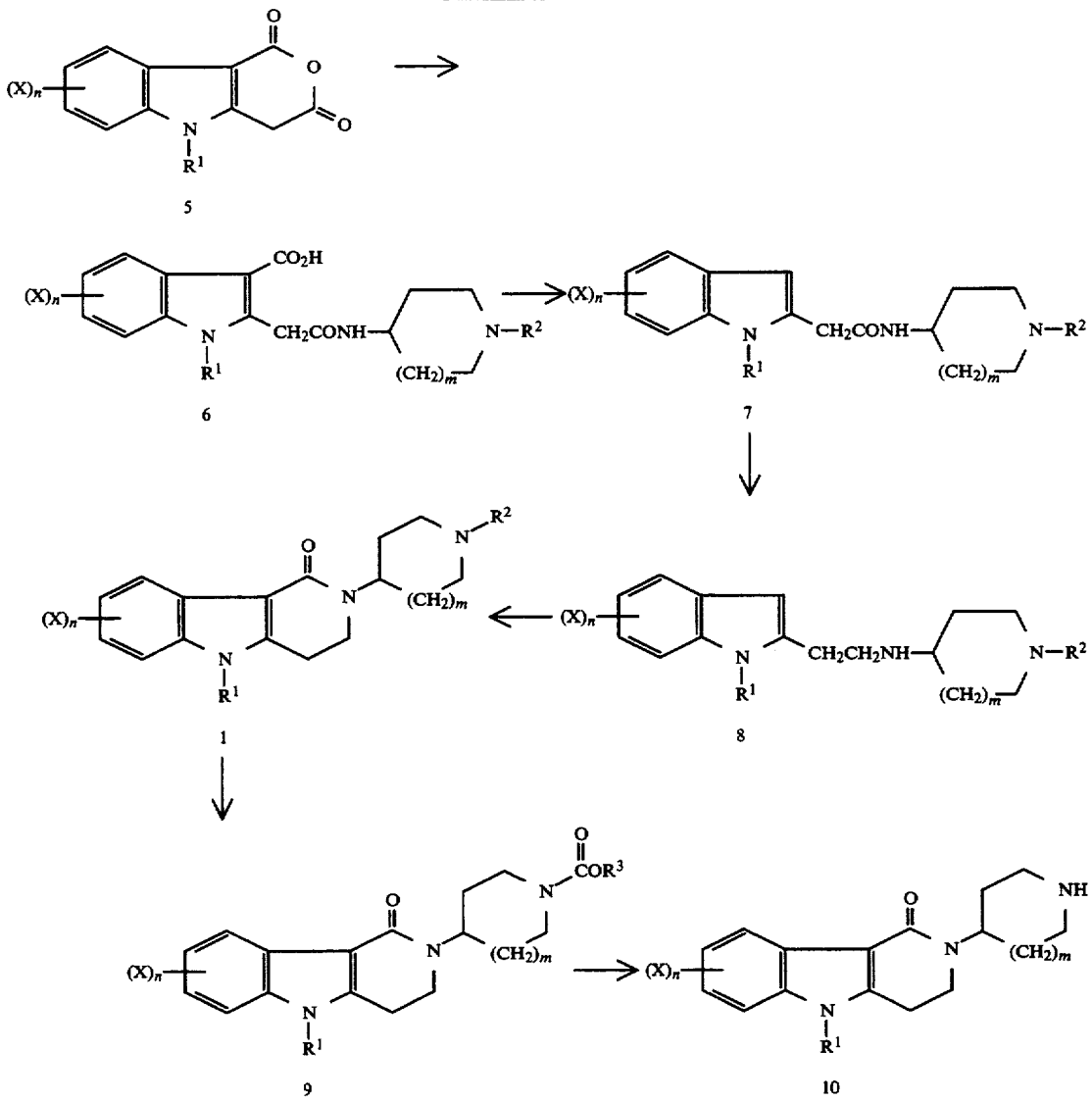

wherein $R^1$, $R^2$, $R^3$, m, and n are as hereinbeforedescribed.

We claim:
1. A compound of the formula

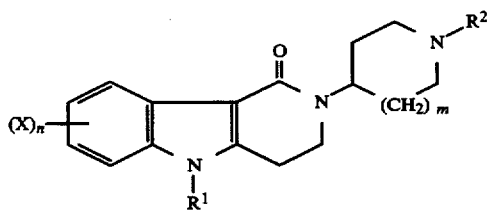

wherein
$R^1$ is hydrogen, loweralkyl, phenyl, phenyl substituted by one or more loweralkyl, loweralkoxy, halogen, or trifluoromethyl groups, phenylloweralkyl or phenylloweralkyl in which the phenyl group is substituted by one or more loweralkyl, loweralkoxy, halogen, or trifluoromethyl groups;

$R^2$ is hydrogen, loweralkyl, furanylloweralkyl, thienylloweralkyl, pyrrolylloweralkyl, pyridinylloweralkyl, phenylloweralkyl, phenylloweralkyl in which the phenyl group is substituted by one or more loweralkyl, loweralkoxy, halogen, or trifluoromethyl groups, or a group of the formula

wherein $R^3$ is loweralkyl, haloloweralkyl, phenyl, phenyl substituted by one or more loweralkyl, loweralkoxy, halogen, or trifluoromethyl groups, phenylloweralkyl, or phenylloweralkyl in which the phenyl group is substituted by one or more loweralkyl, loweralkoxy, halogen, or trifluoromethyl groups;

X is hydrogen, loweralkyl, loweralkoxy, halogen, or trifluoromethyl;

m is 0;

n is 1 or 2; an optical isomer thereof, or a pharmaceutically acceptable salt thereof.

2. A method of treating psychoses comprising administering to a mammal in need of psychoses treatment a psychoses treating effective amount of a compound as defined in claim 1.

3. A psychoses treating composition comprising an inert psychoses treating adjuvant and, as the active ingredient, an amount effective in alleviating psychoses of a compound as defined in claim 1.

* * * * *